(12) United States Patent  
Nozato

(10) Patent No.: US 8,591,029 B2
(45) Date of Patent: Nov. 26, 2013

(54) IMAGING DEVICE AND IMAGING METHOD

(75) Inventor: Koji Nozato, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 130 days.

(21) Appl. No.: 12/945,534

(22) Filed: Nov. 12, 2010

(65) Prior Publication Data

US 2011/0116043 A1    May 19, 2011

(30) Foreign Application Priority Data

Nov. 18, 2009 (JP) ................................. 2009-262550

(51) Int. Cl.
*A61B 3/14* (2006.01)
*A61B 3/00* (2006.01)

(52) U.S. Cl.
USPC ........................... 351/206; 351/200; 351/210

(58) Field of Classification Search
USPC .......... 351/206, 200, 203, 205, 210–211, 221
See application file for complete search history.

(56) References Cited

U.S. PATENT DOCUMENTS

| | | | |
|---|---|---|---|
| 2003/0025874 A1* | 2/2003 | Williams et al. | 351/200 |
| 2003/0048413 A1* | 3/2003 | Ross et al. | 351/211 |
| 2003/0053026 A1* | 3/2003 | Roorda | 351/206 |
| 2004/0189941 A1 | 9/2004 | Bucourt | |
| 2008/0002863 A1 | 1/2008 | Northcott | |
| 2010/0149490 A1* | 6/2010 | Olivier et al. | 351/206 |

FOREIGN PATENT DOCUMENTS

| | | |
|---|---|---|
| JP | H10-216092 A | 8/1998 |
| JP | 2005-501587 A | 1/2005 |
| JP | 2007-515220 A | 6/2007 |
| WO | 01/28411 A1 | 4/2001 |
| WO | 2007/035334 A2 | 3/2007 |
| WO | 2009/024981 A2 | 2/2009 |

OTHER PUBLICATIONS

Y.Zhang et al, "High-speed volumetric imaging of cone photoreceptors with adaptive optics spectral-domain optical coherence tomography", Optics Express, vol. 14, No. 10, May 15, 2006.
B. Hermann et al., "Adaptive-optics ultrahigh-resolution optical coherence tomography", Sep. 15, 2004 / vol. 29, No. 18 / Optics Letter, 2142-2144.
R.J. Zawadzki et al., "Adaptive-optics optical coherence tomography for high-resolution and high-speed 3D retinal in vivo imaging", Oct. 17, 2005 / vol. 13, No. 21 / Optics Express 8532-8546.

* cited by examiner

*Primary Examiner* — Dawayne A Pinkney
(74) *Attorney, Agent, or Firm* — Canon USA Inc IP Division

(57) ABSTRACT

An imaging device includes an illuminating unit configured to illuminate a measurement object with light from a light source; an aberration correcting unit configured to correct aberration of the measurement object occurring in light returning from the measurement object, the returning light being provided by light illuminating the measurement object through an area differing from a center axis of the illuminating unit; and an image obtaining unit configured to obtain an image of the measurement object on the basis of light returning from the measurement object, the returning light being provided by light that is provided after the aberration is corrected by the aberration correcting unit and that illuminates the measurement object through the center axis of the illuminating unit.

17 Claims, 7 Drawing Sheets

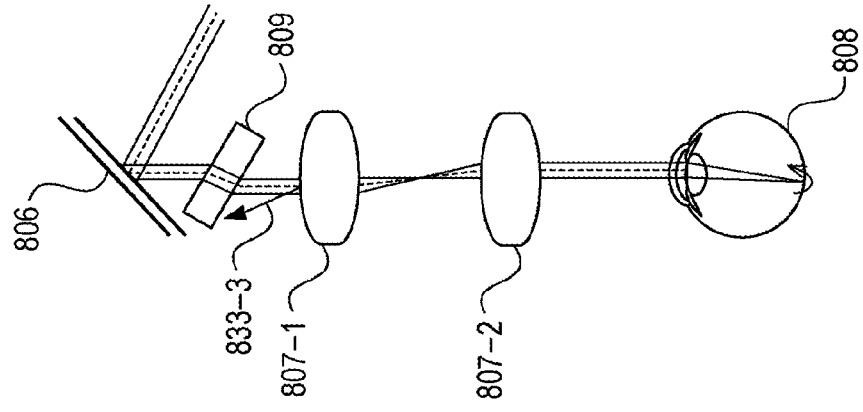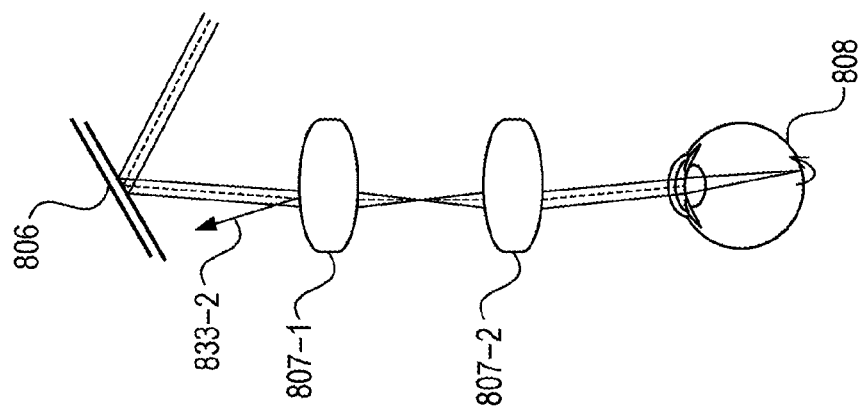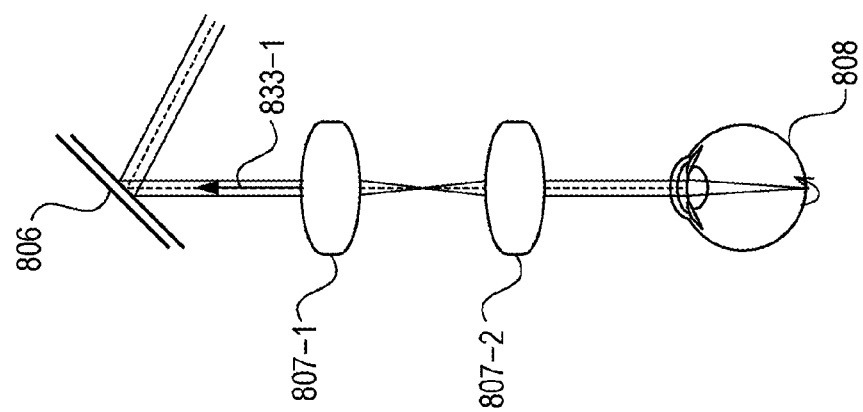

IMAGING DEVICE AND IMAGING METHOD

BACKGROUND OF THE INVENTION

1. Field of the Invention

The present invention relates to an imaging method and a device therefor. More particularly, the present invention relates to an imaging method used in, for example, an ophthalmologic examination, and a device therefor.

2. Description of the Related Art

In recent years, for a device that obtains a tomographic image of a fundus or of the vicinity of the fundus, a scanning laser ophthalmoscope (SLO) or optical coherence tomography (OCT)(optical coherence tomographic device, or optical coherence tomographic method) is used. For the OCT, methods such as a time domain OCT (TD-OCT) (time domain method) and a spectral domain OCT (SD-OCT)(spectral domain method), are available.

When the fundus is photographed by SLO or OCT, the fundus needs to be photographed through an optical structure of an eye, such as a cornea and an eye lens.

An increase in resolution causes aberration of the cornea or the eye lens to greatly influence the quality of a photographed image.

Therefore, research in adaptive optics (AO)-SLO and AO-OCT that is used to provide an optical system with a function of measuring wavefront aberration of an eye and correcting the aberration is being conducted. AO-OCT is discussed by Y. Zhang et al. in Optics Express, Vol. 14, No. 10, 15 May 2006.

In general, AO-SLO and AO-OCT are used to measure the wavefront aberration of an eye with a Shack-Hartmann wavefront sensor system.

In the Shack-Hartmann wavefront sensor system, measurement light is incident upon an eye, and a portion of the light that is reflected is received by a CCD sensor camera through a microlens array, to measure a wavefront. The shape of a deformable mirror is changed so as to correct the measured wavefront, to photograph a fundus through the mirror. It is reported that the resolution of the photographed image is increased in the photographic operation by such a device.

In measuring the wavefront aberration of the eye using adaptive optics, as described above, the measurement light is incident upon the eye, and the portion of the light that is reflected is measured.

However, since the reflectivity of the fundus is very low, and the portion of the light that is reflected by the fundus is very weak, the measurement is greatly affected by stray light from other optical elements that is incident upon the sensor.

Since the measurement light is reflected at a surface of an eyepiece disposed along the way, the reflected light is incident upon the sensor as stray light, thereby considerably reducing measurement precision.

Accordingly, in order to reduce the influence of stray light, a method of forming an optical path from the eye to the sensor with a spherical mirror is disclosed in Vol. 13, No. 21/OPTICS EXPRESS 8532/17 Oct. 2005.

However, when the optical path is formed using the spherical mirror, an optical system becomes very complicated, and the size of the optical system is increased. The spherical mirror itself is required to have high precision, and is very expensive.

Therefore, a structure in which an eyepiece portion is assembled in a lens system is discussed in Vol. 29, No. 18/OPTICS LETTER/15 Sep. 2004. In order to prevent light from being reflected at a surface of a lens, an eyepiece system is formed without passing a center axis of the lens therethrough. The eyepiece system is formed so that a light incidence position is situated away from the center of the lens when measuring wavefront aberration with a wavefront sensor and when obtaining an optical image of a test eye by OCT or SLO.

SUMMARY OF THE INVENTION

Here, since the structure does not use the central portion of the lens not only when measuring the wavefront aberration, but also when obtaining the optical image of the test eye, it becomes difficult to increase field angle, and image quality is reduced due to the influence of lens aberrations. Since the reflectivity of the fundus is not uniform, in the structure in which the central portion of the lens is not used even when obtaining the optical image of the test eye, light that is incident upon and reflected by a wave-aberration sensor becomes unstable, thereby reducing the precision with which the aberrations are measured.

In view of the aforementioned problems, the present invention provides an imaging method which makes it possible to stably measure wavefront aberrations even by using an optical system that uses a central portion of a lens when obtaining an optical image of a test object in performing imaging of the optical image using adaptive optics. In addition, the present invention provides a device therefor. The present invention provides the imaging method and a device therefor having the following structures.

According to an aspect of the present invention, there is provided an imaging device including an illuminating unit configured to illuminate a measurement object with light from a light source; an aberration correcting unit configured to correct aberration of the measurement object occurring in light returning from the measurement object, the returning light being provided by light illuminating the measurement object through an area differing from a center axis of the illuminating unit; and an image obtaining unit configured to obtain an image of the measurement object on the basis of light returning from the measurement object, the returning light being provided by light that is provided after the aberration is corrected by the aberration correcting unit and that illuminates the measurement object through the center axis of the illuminating unit.

According to the present invention, it is possible to provide an imaging method which makes it possible to stably measure wavefront aberrations even by using an optical system that uses a central portion of a lens when obtaining an optical image of a test object in performing imaging of the optical image using adaptive optics; and to provide a device therefor.

Further features of the present invention will become apparent from the following description of exemplary embodiments with reference to the attached drawings.

BRIEF DESCRIPTION OF THE DRAWINGS

FIGS. 4A, 4B, and 4C are schematic views each showing an exemplary light ray at eyepiece portions in the first embodiment of the present invention.

DESCRIPTION OF THE EMBODIMENTS

Next, an exemplary structure of an imaging method and that of an imaging device in an embodiment of the present invention will be described.

However, the present invention is not limited to the structures of the embodiment.

First Embodiment

Figure 1A:
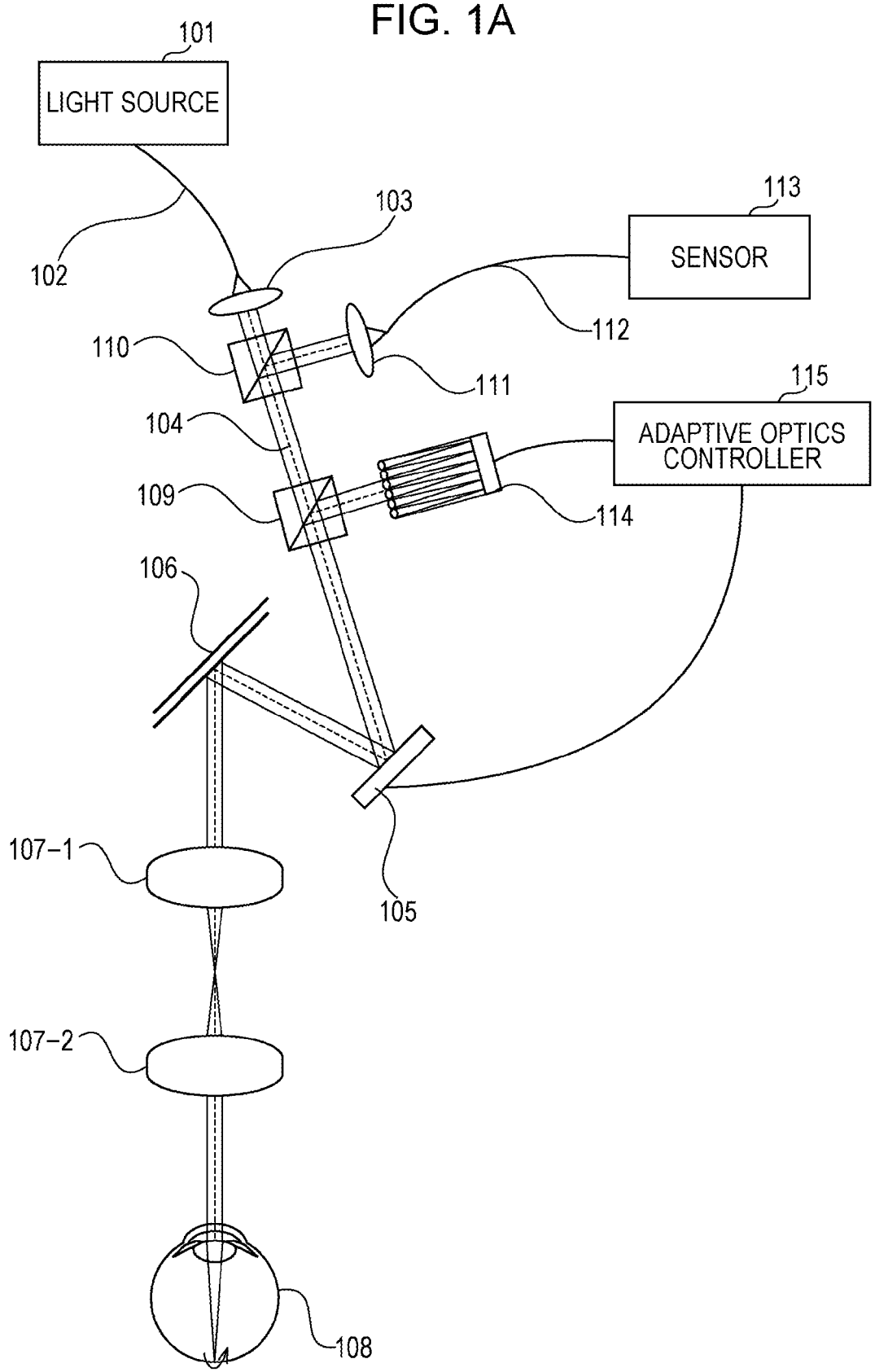
FIGS. 1A and 1B are schematic views illustrating SLO in a first embodiment of the present invention.
Figure 1B:
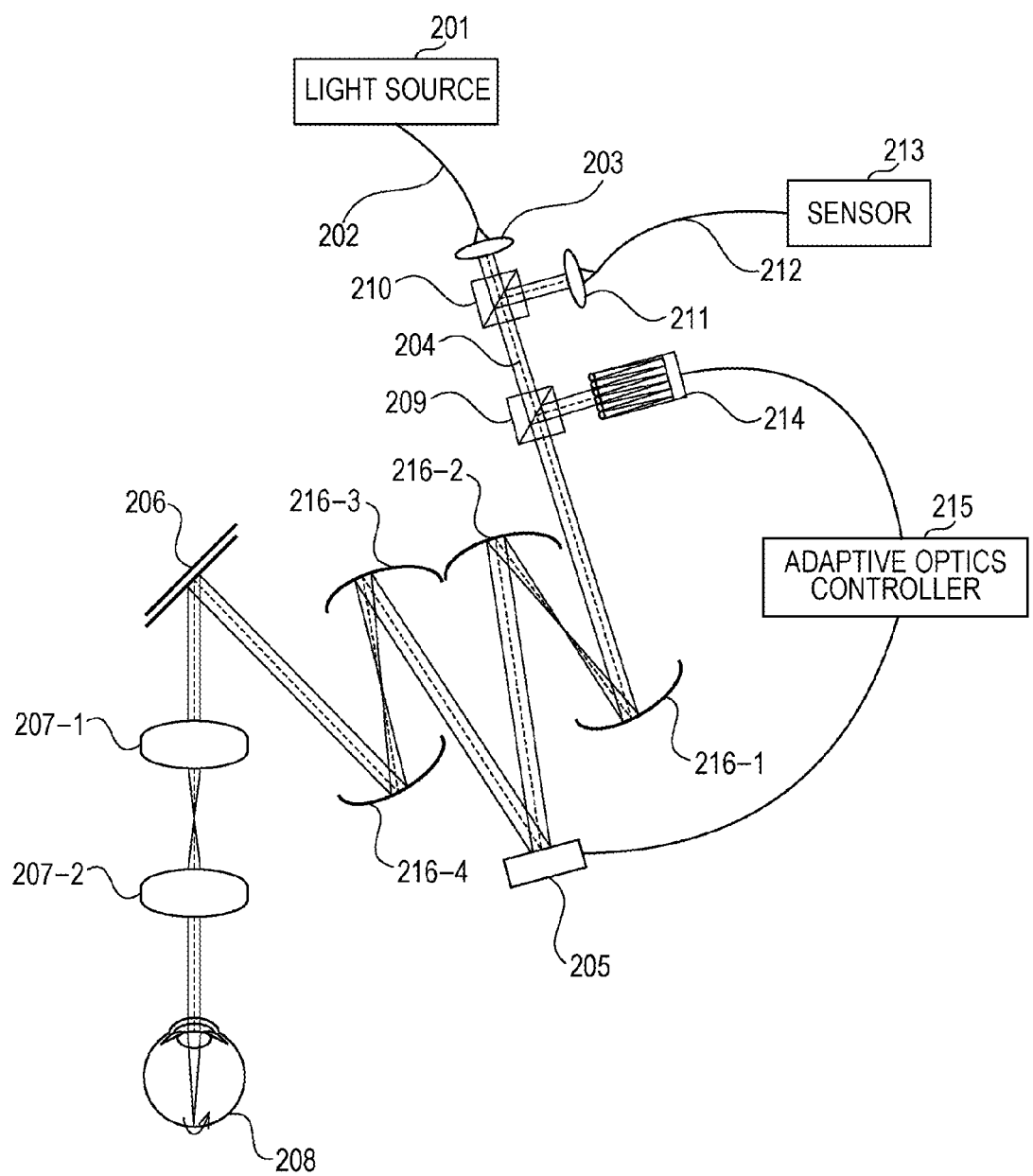

With reference to FIGS. 1A and 1B, a practical form in which an imaging method and a device therefor according to a first embodiment of the present invention are applied to a fundus photographing method (in which a test object is a test eye) and to a device therefor will be described. In the embodiment, a scanning laser ophthalmoscope (SLO) using adaptive optics is used as an example. Even in optical coherent tomography (OCT), the structure of an eyepiece portion is similar.

In FIG. 1A, reference numeral 101 denotes a light source (such as a laser, a low-coherent light source, or SLD). Although the wavelength of the light source 101 is not particularly limited, the wavelength is in the range of from 400 nm to 2 μm.

In particular, a wavelength in the range of from approximately 600 to 1500 nm is used for photographing a fundus. As a wavelength width for use in OCT, for example, a wavelength width of at least 1 nm, desirably, a wavelength width of at least 10 nm, or, more desirably, a wavelength width that is greater than or equal to 30 nm is used.

For example, an ultrashort pulse laser such as a titanium sapphire laser may be used as the light source.

Different light sources may be used for photographing a fundus and for measuring a wavefront, respectively. Lights generated from the respective light sources may be multiplexed along the way (that is, in an optical path from the light source for photographing a fundus to an optical-scanning optical system 106).

Light emitted from the light source 101 passes through an optical fiber 102, is converted into parallel light by a collimator 103, and is used for illumination.

As measurement light 104, the light used for the illumination passes through beam splitters 110 and 109 (serving as light slitting units), and is used for illumination of a deformable mirror 105.

Further, as shown in FIG. 1B, using, for example, optical systems 216-1 and 216-2 (such as spherical mirrors), an optical conjugate state may be adjusted.

The deformable mirror 105 can locally change a reflection direction of the light.

Various types of deformable mirrors 105 are put into practical use.

Figure 2A:
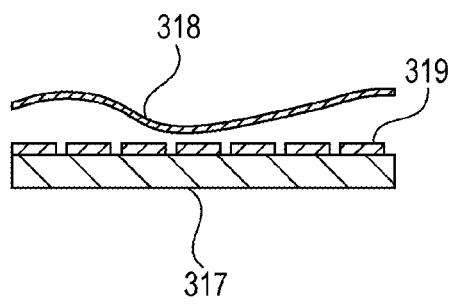
FIG. 2A is a schematic view illustrating a deformable mirror in the first embodiment of the present invention.

For example, a device such as that shown in FIG. 2A is known.

The device includes a membranous mirror surface 318, a base section 317, actuators 319, and a supporting unit (not shown). The mirror surface 318 reflects incident light and is capable of changing its shape. The actuators 319 are disposed between the mirror surface 318 and the base section 317. The supporting unit supports the mirror surface 318 from the vicinity thereof.

In a principle of operating the actuators 319, for example, static electricity or a magnetic force may be used.

The structure of each actuator 319 differs depending upon the principle. The actuators 319 are arranged two-dimensionally on the base section 317. By selectively driving the actuators 319, the mirror surface 318 can freely change its shape.

The measurement light 104 reflected by the deformable mirror 105 is used for a one-dimensional or a two-dimensional scanning operation using the optical-scanning optical system 106.

For the optical-scanning optical system 106, a galvanometer scanner is suitable.

The measurement light used for the scanning operation by the optical-scanning optical system 106 illuminates an eye 108 through an eyepiece 107-1 and an eyepiece 107-2. The measurement light that has illuminated the eye 108 is reflected or scattered by a fundus.

The reflected or scattered light travels in the same path that the incident light travels and in an opposite direction. A portion of the light is reflected to a wavefront sensor 114 by the beam splitter 109, and is used to measure a wavefront of the light ray.

As the wavefront sensor (a wavefront aberration measuring unit) 114 that measures aberrations occurring at a test eye, for example, a Shack-Hartmann sensor is suitable.

Figure 2B:
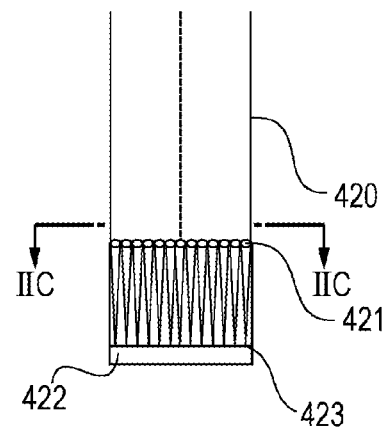
FIGS. 2B and 2C are schematic views each showing a structure of a wavefront sensor.
Figure 2C:
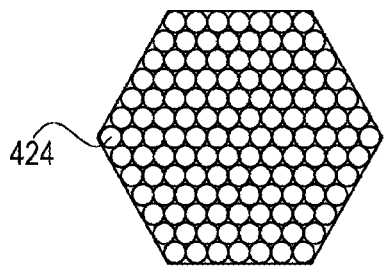

FIGS. 2B and 2C are schematic views of the Shack-Hartmann sensor.

Reference numeral 420 denotes a light ray used to measure wavefront aberration (wavefront aberration measurement light). The light ray 420 passes through a microlens array 421, and is focused on a focal point 423 on a CCD sensor 422.

FIG. 2C shows the wavefront sensor from a position indicated by IIC-IIC in FIG. 2B. The microlens array 421 is shown as including a plurality of microlenses 424.

Since the light ray 420 is focused on the CCD sensor 422 through each microlens 421, the light ray 420 is divided into spots corresponding in number to the number of microlenses 421, and is focused.

Figure 2D:
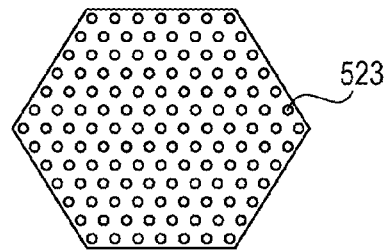
FIGS. 2D, 2E, and 2F are schematic views each showing an exemplary result of measurement using the wavefront sensor.

FIG. 2D shows a state in which the spots are focused on the CCD sensor 422.

Each microlens focuses the light on its corresponding spot 523. The number of spots 523 that are formed is equal to the number of microlenses.

Figure 2E:
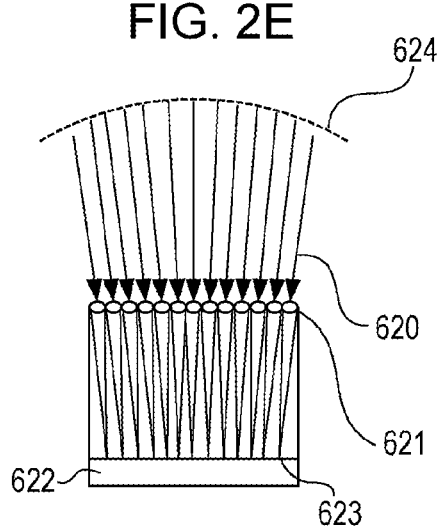
Figure 2F:
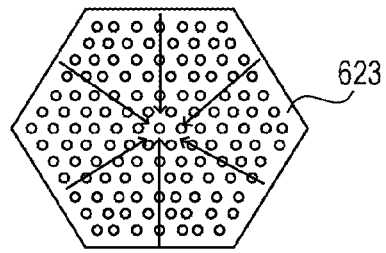

The wavefront of the light ray that is incident from the position of each spot 523 is calculated. For example, FIG. 2E is a schematic view showing a case in which a wavefront having spherical aberration is measured. Each light ray 620 is formed at a wavefront denoted by reference numeral 624. Each light ray 620 is focused to a localized position of the wavefront in a vertical direction by the microlens array 621. A focused state of the CCD sensor 622 in this case is shown in FIG. 2F.

Since each light ray 624 has spherical aberration, each spot 623 is focused so as to be inclined towards a central portion. The wavefront 624 of each light ray 620 can be known by calculating the inclined position.

A portion of the reflected/scattered light that has passed the beam splitter 109 is reflected by the beam splitter 110, and is guided to a light-intensity sensor 113 through a collimator 111 and an optical fiber 112.

The light-intensity sensor 113 converts the light into an electrical signal, and a computer (not shown) forms it into an image (fundus image).

Here, the wavefront sensor 114 is connected to an adaptive optics controller 115, and transmits the wavefront of the received light ray to the adaptive optics controller 115.

The deformable mirror 105 is also connected to the adaptive optics controller 115, and is formed into the shape specified by the adaptive optics controller 115.

On the basis of the wavefront obtained from the wavefront sensor 114, the adaptive optics controller 115 calculates a shape that corrects the wavefront to a wavefront not having aberrations, and gives an instruction to the deformable mirror 105 to change its shape to the calculated shape.

Here, it is necessary to calculate the aberrations by receiving the reflected/scattered light from the fundus by the wavefront sensor 114. In the related art, light reflected at the surface of each of the eyepieces 107-1 and 107-2 enters the wavefront sensor 114, as a result of which the precision with which the aberrations is measured is considerably reduced.

Figure 3:
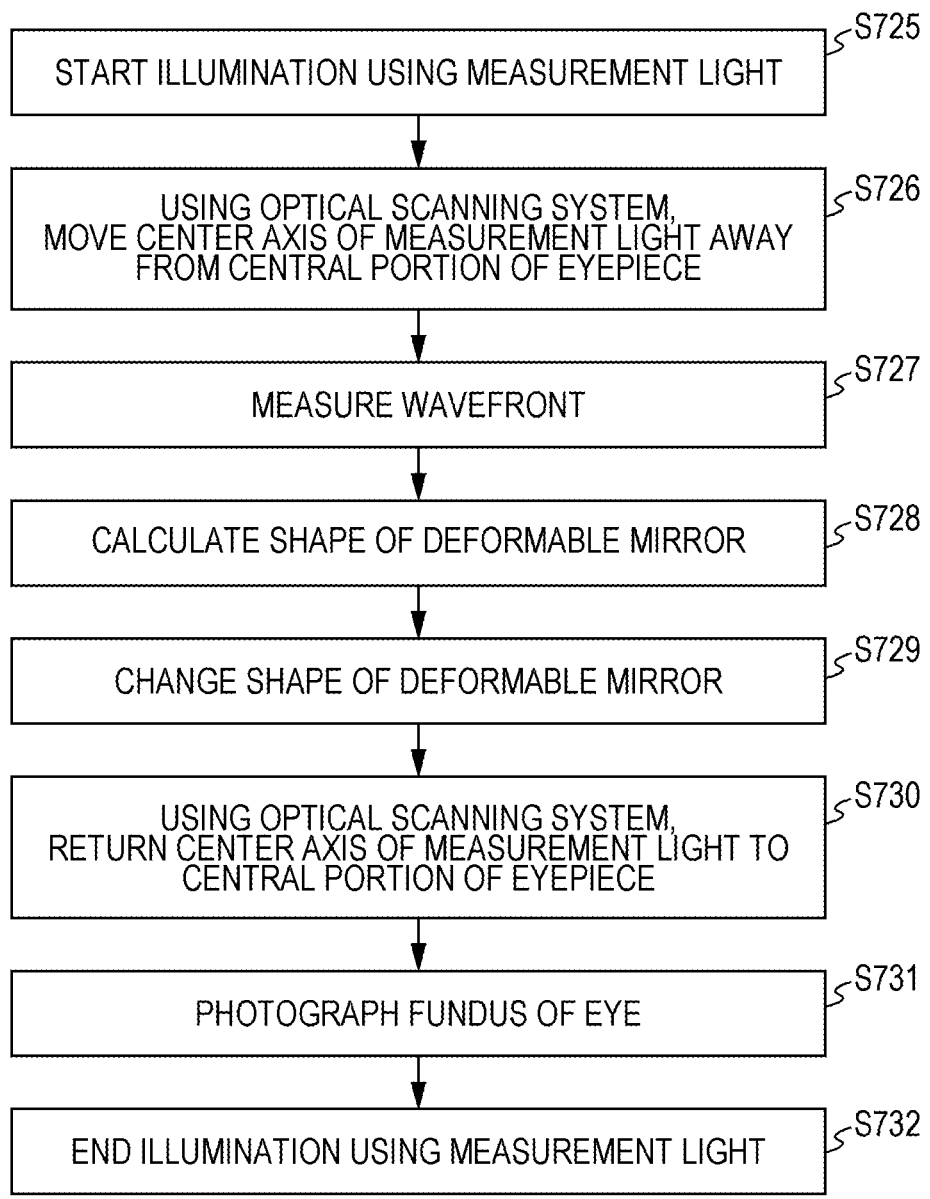
FIG. 3 is a flowchart of an exemplary control step in the first embodiment of the present invention.

Accordingly, in the embodiment, the aberrations are measured by steps such as those shown in FIG. 3.

In Step 725, illumination using measurement light from the light source 101 is started.

Then, in Step 726, a test object is illuminated through an area in which the center axis of the measurement light (wavefront aberration measurement light) is shifted from the center axis of the eyepieces 107 by the optical-scanning optical system 106, so that wavefront aberration is measured.

For example, the angle at which the light ray illuminates the eyepieces 107 is changed by a very small amount by moving the optical-scanning optical system 106.

An amount of change of the angle depends upon the curvature of the surface of each eyepiece 107 and the distance to the wavefront sensor. However, if, for example, the distance to the wavefront sensor using a 1-mm light ray is at least 100 mm, the light ray is moved in one direction by approximately 0.5 degrees. Here, although the light is reflected at the surface of each eyepiece 107 in a path differing from that taken by the incident light, the reflected/scattered light from the fundus is bent again by the optical-scanning optical system 106. Therefore, the light returns in the same path as that taken by the incident light, and is incident upon the wavefront sensor.

Next, in Step 727, the wavefront of the reflected/scattered light from the eye is measured.

Even if the angle of incidence with respect to the eye changes by a very small amount, aberrations of the eye do not change considerably.

On the basis of the measured wavefront, in Step 728, the shape of the deformable mirror 105 is calculated. On the basis of the calculated result (measurement result), in Step 729, the shape of the deformable mirror 105 is changed.

After correcting the aberrations with the deformable mirror 105, in Step 730, the optical-scanning optical system 106 returns the center axis of the measurement light to the central portion of each eyepiece 107. That is, the optical-scanning optical system 106 is returned to its original position so as to allow the measurement light ray to pass through the central portion of each eyepiece. Then, in Step 731, the measurement light is used for a scanning operation with the optical-scanning optical system 106, to photograph a fundus. Then, the illumination using the light ray ends in Step 732. If necessary, Steps 726 to 731 are repeated.

Using FIGS. 4A to 4C, light rays near an eyepiece 807 (807-1) in these steps will be described.

In Step 726, prior to operating an optical-scanning optical system 806, as shown in FIG. 4A, reflected light 833-1 at a surface of the eyepiece 807 is returned along substantially the same path as that taken by an incident light. The returned light is also incident upon a wavefront sensor, thereby reducing the precision with which the wavefront is measured.

In Step 726, by moving the optical-scanning optical system 806, as shown in FIG. 4B, a measurement light ray is controlled so as to move the optical axis of wave-aberration measurement light away from the center axis of the eyepiece.

In FIG. 4B, reflected light 833-2 at the surface of the eyepiece 807-1 is reflected in a path differing from that taken by the incident light, so that the reflected light 833-2 is not incident upon the wavefront sensor.

An optical element that shifts the optical axis of the eyepiece 807 may be made insertable into or removable from a space between the eyepiece 807 and the optical-scanning optical system (a scanning unit) 806 used to perform a scanning operation using the measurement light.

For example, as shown in FIG. 4C, there may be formed a structure in which, when aberrations are measured, a parallel plate (such as glass) 809 is inserted at a certain angle to shift the optical axis, so that reflected light from the surface of the eyepiece is eliminated.

When photographing a fundus, the parallel plate 809 is moved to a position where the light is not incident upon the parallel plate 809, and the parallel plate 809 is removed from between the optical-scanning optical system 806 and the eyepiece 107, to return the optical axis to the eyepiece center (that is, to the state shown in FIG. 4A).

The optical axis after the light impinges upon the parallel plate 809 needs to be parallel to the optical axis before the light impinges upon the parallel plate 809.

In the case shown in FIG. 4C, since the position of the optical axis is shifted by inserting the parallel plate 809, it is necessary to adjust the position of the wavefront sensor accordingly. In addition, since aberration of an optical system is changed by inserting the parallel plate 809, it is necessary to previously determine aberration resulting from the parallel plate 809 and to subtract the aberration of the parallel plate 809 when photographing the fundus.

Alternatively by disposing the parallel plate 809 closer to a light exit side than the wavefront sensor, the aforementioned problem is eliminated.

The present is not limited to the above-described exemplary structure. As long as the position where light is incident upon the eyepiece is changeable, any structure may be used.

The parallel plate may be any member as long as its refractive index differs from that of the outside and passes light therethrough.

In the exemplary structure shown in FIG. 3, Steps 727, 728, and 729 are only performed once. However, these steps may be repeated until an aberration amount becomes less than or equal to a certain value.

In addition, Steps 727, 728, and 729 may be performed using an optical scanning unit at an optical path differing from an optical path for photographing the fundus, with portion of the optical path for photographing the fundus and that for measuring a wavefront being formed as separate optical paths.

In Step 727 in which the wavefront is measured, when the optical scanning optical system performs a very slight scanning operation within a range in which the center of the eyepiece is not passed, ununiform reflection from the fundus can be reduced.

Accordingly, aberrations are corrected when a light ray reflected/scattered from an eye passes the deformable mirror 105, so that the efficiency with which the light is received by the light-intensity sensor 113 is increased, and sensitivity and resolution are increased.

Second Embodiment

Figure 5:
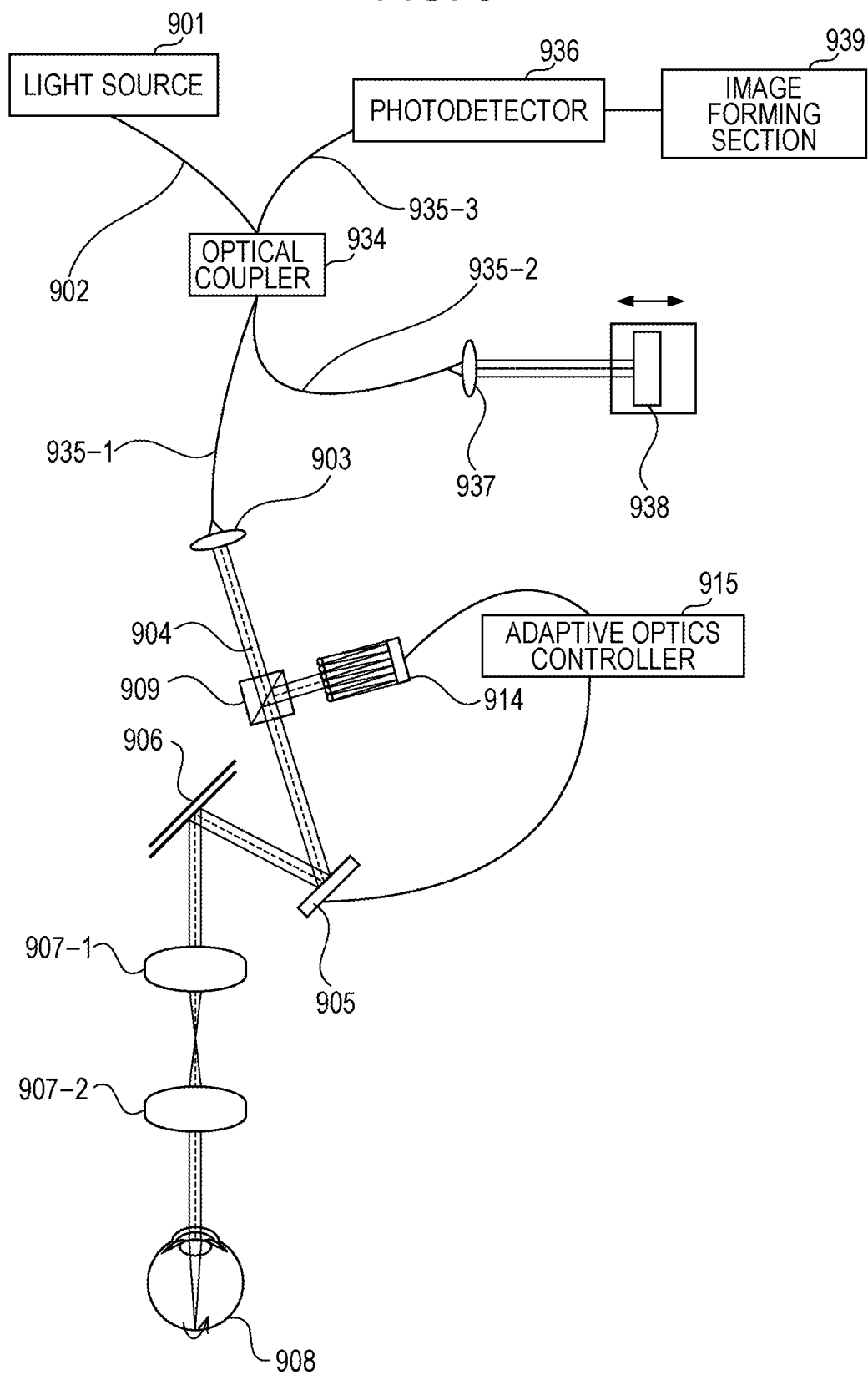
FIG. 5 is a schematic view illustrating OCT in a second embodiment of the present invention.

With reference to FIG. 5, a practical form in which an imaging method and a device therefor according to a second embodiment of the present invention are applied to a fundus photographing method (in which a test object is a test eye) and to a device therefor will be described. In the embodiment, an OCT device using adaptive optics is used as an example.

Light emitted from a light source 901 passes through an optical fiber 902, and is divided into signal light and reference light by an optical coupler 934.

The signal light passes through an optical fiber 935-1, is guided to a collimator 903, becomes parallel light, and is used for illumination as measurement light 904.

The measurement light 904 used for the illumination passes through a path that is similar to that in the first embodiment, and reaches an eye 908. As in the first embodiment, the light that is reflected/scattered by the eye is guided to a wavefront sensor 914 and a collimator 903.

On the basis of aberration measured at the wavefront sensor 914, the shape of a deformable mirror 905 is changed, to correct the aberration of the eye. The light converged at the collimator 903 is guided back to the optical coupler 934 through the fiber 935-1.

In contrast, the reference light is guided to a collimator 937 through an optical fiber 935-2, and illuminates a reference mirror 938.

Since the reference mirror 938 adjusts an optical path length of the reference light, it includes a mechanism that moves back and forth in an optical axis direction.

The reference light reflected by the reference mirror 938 is converged at the collimator 937 again, and is guided to the optical coupler 934 again by the optical fiber 935-2.

The signal light and the reference light guided to the optical coupler 934 are multiplexed at the optical coupler 934, and are guided to a photodetector 936 through an optical fiber 935-3, so that the intensity of interference light is measured.

At an image forming section 939, a three-dimensional image or a tomographic image of a fundus is formed from the intensity of the interference light measured at the photodetector 936, the position of the reference mirror 938, and the position of an optical-scanning optical system 906.

In another embodiment, aberrations are corrected in real time even during a photographic operation.

The actual OCT photographic operation often requires a certain amount of time for a focusing operation, adjusting a photographic position, a photographic operation, etc.

Aberrations of an eye are changed any time when refraction at the eye is adjusted and a tear layer of the eye is changed. When it takes time to perform the photographic operation, aberrations that need to be corrected change even during the photographic operation. Therefore, even during the photographic operation, it is necessary to measure the wavefront and change the shape of the deformable mirror 905.

Accordingly, in the embodiment, even during the photographic operation, the wavefront sensor 914 and the deformable mirror 905 continue to operate, thereby making it possible to maintain a suitable correction state at all times.

By the optical-scanning optical system 906, the retina is scanned with measurement light. When a central portion of the eyepiece 907 is scanned, measurement carried out by the wavefront sensor 914 is stopped. The measurement is performed at times other than when the central portion of the eyepiece 907 is scanned. A method of controlling the deformable mirror on the basis of information of the wavefront sensor is similar to that in the first embodiment.

The operation of the wavefront sensor 914 is described with reference to FIGS. 4D and 4E.

Figure 4D:
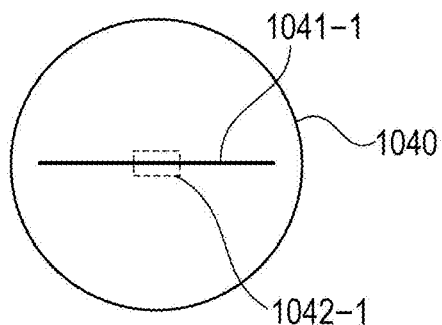
FIGS. 4D and 4E are schematic views each showing an optical scanning and a wavefront measurement range.

FIG. 4D shows a case in which a B scan for photographing a tomographic image of a fundus is performed.

Figure 4E:
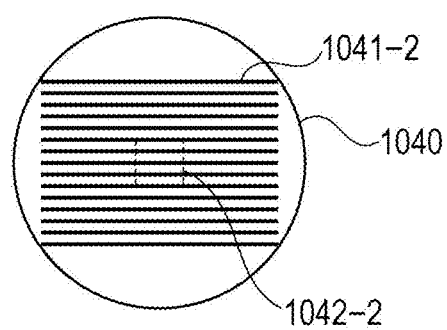

FIG. 4E shows a case in which a C scan for photographing a planar image of a fundus having a particular depth is performed.

Reference numeral 1040 denotes a surface of the eyepiece 907 at a side of the optical-scanning optical system 906.

First, in FIG. 4D, a range denoted by reference numeral 1041-1 is scanned with the measurement light 904 using the optical-scanning optical system 906.

Here, when the measurement light enters the range 1042-1 at the central portion of the lens, measurement by the wavefront sensor 914 is stopped, and is performed at times other than when the measurement light enters the range 1042-1.

This also applied to the case shown in FIG. 4E. The measurement light is used for a scanning operation in a plane and in a range 1041-2. When a range 1042-2 is used, measurement by the wavefront sensor 914 is stopped. The measurement is performed at times other than when this range is scanned.

Accordingly, when the measurement using wavefront aberration measurement light scans an area other than the central axis of the eyepiece, the influence of stray light resulting from reflection at the surface of the eyepiece is eliminated, thereby making it possible to measure a wavefront with high precision.

The embodiment is not limited to OCT, so that it is applicable to an ophthalmologic device such as SLO.

EXAMPLES

Examples of the present invention will hereunder be described.

Example 1

As Example 1, a structural example applied to a scanning laser ophthalmoscope (SLO) will be described. The structure of the SLO in the example is basically the same as that of the SLO in the first embodiment, so that it will be described with reference to FIG. 1.

Although the example is a case applied to the scanning laser ophthalmoscope (SLO), the present invention is not limited to the SLO.

First, light emitted from a light source 101 is guided to a single-mode optical fiber 102, and light emitted from a fiber end is converted into parallel light by a collimator lens 103. The parallel light passes through a splitting optical system 110, and is used for illumination as measurement light 104. The light source is, for example, a semiconductor laser, a He—Ne laser, or an Ar laser. Its illumination power is adjusted in accordance with the wavelength.

The measurement light 104 passes through another beam splitter 109, and is reflected by a deformable mirror 105. The reflected light is used for a scanning operation by an optical-scanning optical system 106.

The optical-scanning optical system 106 causes a principal light ray of the measurement light to be inclined with respective to an optical axis at inclination angles in two orthogonal directions.

By this, a light beam that has passed through eyepieces 107-1 and 107-2 scans a pupil (iris) of an eye at an angle.

As a result, by optical action of the eye, an observation fundus portion 108 is scanned in a vertical plane (x-y plane) in an optical direction (depth direction) along the fundus.

Although a galvanometer scanner is used for the optical-scanning optical system 106, for example, a polygonal mirror may also be used.

By moving the eyepiece 107-1 or the eyepiece 107-2 in the optical axis direction, a proper diopter of the eye can be provided.

Of reflected light and backwardly scattered light from the observation fundus portion 108, light traveling in a direction opposite to that of the incident light through substantially the same optical path taken when the light is incident upon the observation fundus portion 108 passes the optical-scanning optical system 106, and is reflected by the deformable mirror 105.

The beam splitter 109 reflects a portion of the light reflected by the deformable mirror 105 to a wavefront sensor 114, and transmits a remaining portion thereof towards the beam splitter 110.

A portion of the light is reflected towards a collimator 111 by the beam splitter 110. The light converged at the collimator 111 reaches a light-intensity sensor 113 through an optical fiber 112, is converted into an electrical signal, and is formed into an image by a control computer (not shown).

An avalanche photodiode is used for the light-intensity sensor 113. For the wavefront sensor 114, a Shack-Hartmann sensor is used. For the deformable mirror 105, a thin-film mirror that is driven by static electricity is used.

Next, in the example, a measurement step will be described.

First, a shutter (not shown), provided in a measurement-light optical path, is opened, and illumination of an eye with measurement light is started.

Next, the optical-scanning optical system 106 is moved upward with respect to the eye by one degree, to measure a wavefront with the wavefront sensor 114.

Exemplary items of information regarding the measured wavefront are shown in FIGS. 4F to 4I as in Example 1.

Figure 4F:
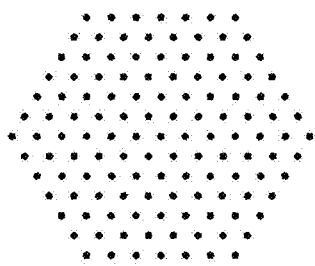
FIGS. 4F, 4G, 4H, and 4I are schematic views each showing exemplary aberration in an embodiment of the present invention.

FIG. 4F shows a Shack-Hartmann photographed image.

Figure 4G:
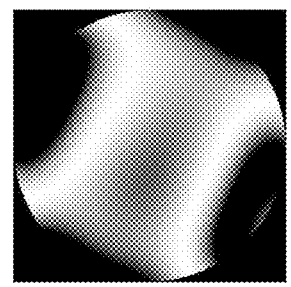

From the position of each spot, aberration information is calculated, and aberration data such as that shown in FIG. 4G is obtained. This is a graph showing the magnitude of aberration. When a point spread function for a case in which light is converged at one point is calculated on the basis of the aberration, the calculated result is approximately a Strehl ratio that is equal to 0.01.

From the aberration data, the shape for correcting the wavefront is calculated, and an instruction is given to the deformable mirror 105 to drive the deformable mirror 105.

Figure 4H:
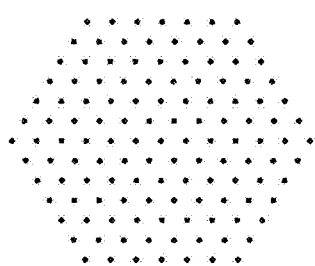

Further, the measurement and control are repeated at 10 Hz/s. After 5 seconds, a Shack-Hartmann photographed image such as that shown in FIG. 4H is obtained.

Figure 4I:
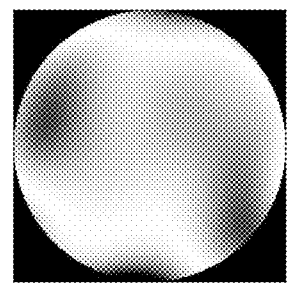

When the aberration is calculated on the basis of this image, aberration data is as shown in FIG. 4I. The Strehl ratio is 0.6.

Accordingly, while maintaining the shape of the deformable mirror 105 as a result of stopping the operation of the wavefront sensor, the optical-scanning optical system 106 is returned to a central portion, and scans a range of 20 degrees in an up-down direction and a left-right direction including the center, to photograph a fundus. As a result, a photographic operation of high sensitivity is capable of being performed.

Example 2

Next, an Example 2 is described.

In Example 2, a structural example is also applied to a scanning laser ophthalmoscope (SLO), and a planar image of a retina is obtained. The structure of a device is similar to that in Example 1.

In Example 2, a method of correcting aberration is performed while obtaining the planar image.

As in Example 1, measurement light from a light source is used for a scanning operation using an optical-scanning optical system, to illuminate a fundus with the measurement light.

In Example 2, in order to perform a photographic operation with high resolution, a range of 20°×20° is photographed for approximately two seconds, and approximately 10 photos are continuously taken.

During 2 to 20 seconds, an aberration state of an eye is changed. Therefore, a wavefront is measured and corrected at all times.

First, a shutter (not shown), provided in a measurement-light optical path, is opened, and illumination of an eye with measurement light is started.

Next, the optical-scanning optical system 106 is moved upward with respect to the eye by one degree, to measure a wavefront with a wavefront sensor 114.

Exemplary items of information regarding the measured wavefront are shown in FIGS. 4F to 4I.

FIG. 4F shows a Shack-Hartmann photographed image.

From the position of each spot, aberration information is calculated, and aberration data such as that shown in FIG. 4G is obtained. This is a graph showing the magnitude of aberration. When a point spread function for a case in which light is converged at one point is calculated on the basis of the aberration, the calculated result is approximately a Strehl ratio that is equal to 0.01. From the aberration data, the shape for correcting the wavefront is calculated, and an instruction is given to a deformable mirror 105 to drive the deformable mirror 105.

Further, the measurement and control are repeated at 10 Hz/s. After 5 seconds, a Shack-Hartmann photographed image such as that shown in FIG. 4H is obtained. When the aberration is calculated on the basis of this image, aberration data is as shown in FIG. 4I. The Strehl ratio is 0.6.

Accordingly, scanning using the optical-scanning optical system 106, and photographing of the fundus are started.

With respect to the eye, a lateral direction corresponds to a main scanning direction, and a vertical direction corresponds to a sub scanning direction. A main scanning operation is performed at 500 Hz, and a sub scanning operation is performed at 0.5 Hz. A scanning range is 20 degrees in an up-down direction and 20 degrees in a left-right direction including the center.

Even during a photographic operation, the wavefront sensor 114 and the deformable mirror 105 are continuously operated. However, when the sub scanning is in a range of ±1° from the center, the measurement using the wavefront sensor is stopped, and the shape of the deformable mirror is maintained.

In ranges other than the range of ±1°, the measurement using the wavefront sensor 114 is performed, and the deformable mirror 105 is controlled to a shape that is in accordance with measured aberration information.

In this way, for example, imaging of an optical image and measurement of wavefront aberration are made to progress simultaneously, and 10 photographs of the fundus are continuously taken. The photographic operation provides high sensitivity and very high image quality.

According to the fundus photographing method and device according to the embodiments and examples described above, it is possible to perform a photographic operation providing high sensitivity and very high image quality in various types of fundus photographing devices using SLO or OCT even for an eye having aberrations.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-262550 filed Nov. 18, 2009, which is hereby incorporated by reference herein in its entirety.

What is claimed is:

1. An imaging device comprising:
an illuminating unit configured to illuminate a measurement object with light from a light source;
an aberration correcting unit configured to correct aberration of the measurement object on the basis of first returning light from the measurement object, the first returning light being provided by the light from the light source illuminating the measurement object, the light from the light source illuminating the measurement object through an area differing from a center axis of the illuminating unit; and
an image obtaining unit configured to obtain an image of the measurement object on the basis of second returning light from the measurement object, the second returning light being provided by the light from the light source that is provided after the aberration is corrected by the aberration correcting unit and that illuminates the measurement object through the center axis of the illuminating unit.

2. The imaging device according to claim 1, further comprising a switching unit configured to switch an illumination position of the light from the light source between the area differing from the center axis of the illuminating unit and an area including the center axis.

3. The imaging device according to claim 2, further comprising a scanning unit configured to perform scanning with the light from the light source,
wherein the switching unit controls the scanning unit so that the illumination position of the light from the light source is switched between the area differing from the center axis of the illuminating unit and an area including the center axis.

4. The imaging device according to claim 2, further comprising a scanning unit configured to perform scanning with the light from the light source, and an optical unit configured to be inserted and removed from between the scanning unit and the illuminating unit,
wherein the switching unit causes the optical unit to be inserted and removed so that the illumination position of the light from the light source is switched between the area differing from the center axis of the illuminating unit and an area including the center axis.

5. The imaging device according to claim 1, further comprising an aberration measuring unit configured to measure the aberration of the measurement object,
wherein the aberration correcting unit is controlled on the basis of a result of measurement of the aberration measuring unit.

6. The imaging device according to claim 1, wherein the measurement object is an eye,
wherein the aberration occurs at an anterior segment of the eye, and
wherein the aberration correcting unit is disposed at an optical conjugate position with respect to the anterior segment of the eye.

7. The imaging device according to claim 1, further comprising a dividing unit configured to divide the light from the light source into reference light and light illuminating the measurement object by the illuminating unit,
wherein the image obtaining unit obtains a tomographic image of the measurement object on the basis of interference light obtained by interference between the reference light and the second returning light.

8. An imaging method comprising:
a first illumination step of illuminating a measurement object with light from a light source through an area differing from a center axis of an illuminating unit;
an aberration correction step of correcting aberration of the measurement object by an aberration correcting unit on the basis of first returning light from the measurement object, the first returning light being provided by the light used for the illumination in the first illumination step;
a second illumination step of illuminating, through the center axis of the illuminating unit, the measurement object with the light from the light source that is provided after the aberration is corrected in the aberration correction step; and
an image obtaining step of obtaining an image of the measurement object on the basis of second returning light from the measurement object, the second returning light being provided by the light used for the illumination in the second illumination step.

9. The imaging method according to claim 8, further comprising an aberration measurement step of measuring the aberration of the measurement object,
wherein the aberration correction step includes controlling the aberration correcting unit on the basis of a result of measurement of the aberration measurement step.

10. The imaging method according to claim 8, wherein the first illumination step includes controlling a scanning unit configured to perform scanning with the light from the light source, and illuminating the area differing from the center axis of the illuminating unit with the light from the light source.

11. The imaging method according to claim 8, wherein the first illumination step includes inserting an optical unit between the illuminating unit and a scanning unit configured to perform scanning with the light from the light source, and
wherein the second illumination step includes removing the optical unit from between the scanning unit and the illuminating unit.

12. The imaging method according to claim 10, wherein the aberration of the measurement object is corrected by the aberration correcting unit, the aberration occurring in light returning from the measurement object, the returning light being provided by light used for illumination when an area other than the center axis of the illuminating unit is scanned by the scanning unit in the second illumination step.

13. A non-transitory computer readable medium encoded with instructions for an apparatus to perform the method recited in claim 8.

14. The imaging device according to claim 1, wherein the illumination unit further comprises a lens.

15. The imaging device according to claim 1, wherein the aberration correction unit is a deformable mirror.

16. An imaging device comprising:
- a lens configured to illuminate a measurement object with light from at least one of a first light source and a second light source;
- an aberration correcting unit configured to correct aberration of the measurement object on the basis of first returning light from the measurement object, the first returning light being provided by the light from the first light source illuminating the measurement object, the light from the first light source illuminating the measurement object through a second position of the lens farther from a center of the lens than a first position of the lens including the center of the lens; and
- an image obtaining unit configured to obtain an image of the measurement object on the basis of second returning light from the measurement object, the second returning light being provided by the light from the second light source that is provided after the aberration is corrected by the aberration correcting unit and that illuminates the measurement object through the first position.

17. An imaging device comprising:
- a light source;
- a scanning unit configured to perform scanning with the light from the light source;
- a lens disposed in an optical path connecting the light source and a measurement object and configured to illuminate the measurement object with light from the light source, scanning being performed with the light by the scanning unit;
- an aberration obtaining unit configured to obtain aberration of the measurement object on the basis of returning light from the measurement object; and
- an image obtaining unit configured to obtain an image of the measurement object on the basis of returning light from the measurement object, wherein the aberration obtaining unit is configured to stop obtaining aberration of the measurement object and the image obtaining unit is configured to obtain an image of the measurement object in a case where the measurement object is illuminated with light with which scanning is performed by the scanning unit through a first range of the lens including a center of the lens, and wherein the aberration obtaining unit is configured to measure aberration of the measurement object and the image obtaining unit is configured to obtain an image of the measurement object, aberration of which is corrected on the basis of a measurement result of aberration measured by the aberration obtaining unit in a case where the measurement object is illuminated with light with which scanning is performed by the scanning unit through a second range of the lens different from the first range.

* * * * *